United States Patent [19]

Jurd

[11] 3,973,040

[45] Aug. 3, 1976

[54] CERTAIN CINNAMYL PHENOLS AS GROWTH INHIBITORS FOR MOSQUITO LARVAE

[75] Inventor: Leonard Jurd, Berkeley, Calif.

[73] Assignee: The United States of America as represented by the Secretary of Agriculture, Washington, D.C.

[22] Filed: July 8, 1975

[21] Appl. No.: 594,168

[52] U.S. Cl. ............................................... 424/346
[51] Int. Cl.² ........................................... A01N 9/26
[58] Field of Search ..................................... 424/346

[56] References Cited
UNITED STATES PATENTS 3,745,222   7/1973   Jurd et al. ........................... 424/346
3,775,541   11/1973  Jurd et al. ........................... 424/346
3,865,748   2/1975   Jurd et al. ........................... 424/346

*Primary Examiner*—V. D. Turner
*Attorney, Agent, or Firm*—M. Howard Silverstein; David G. McConnell

[57] ABSTRACT

Poly-t-butyl-cinnamyl phenols and poly-t-butyl-dihydrocinnamyl phenols are disclosed to be useful for inhibiting the growth of mosquito larvae, thus providing means for controlling mosquito populations.

12 Claims, No Drawings

CERTAIN CINNAMYL PHENOLS AS GROWTH INHIBITORS FOR MOSQUITO LARVAE

Certain of the compounds used in accordance with this invention (e.g., 4,6-di-t-butyl-2-cinnamylphenol) are described and claimed in my copending application Ser. No. 561,583, filed Mar. 24, 1975.

DESCRIPTION OF THE INVENTION

The invention relates to and has among its objects the provision of novel compounds and novel processes for controlling mosquito populations, particularly by inhibiting the growth of mosquito larvae. Further objects of the invention will be evident from the following description wherein parts and percentages are be weight unless otherwise specified.

The abbreviation ppm. used herein refers to parts per million. The symbol $\phi$ is used herein to represent the phenyl

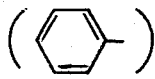

group,

Currently, there are various means for controlling insect populations. For example, one may apply an insecticide to insects or to their habitat. This method of control, however, has the disadvantage that the insecticide may cause harm to humans, animals, and useful insects (bees, for instance). Biological control of insects may be attained by employing compounds which serve as anti-procreants (chemosterilants or oviposition inhibitors).

Another means for controlling insect populations involves the use of compounds which inhibit the growth of the insect larvae. Such compounds are often referred to in the art as juvenile hormone mimics. These agents do not kill the larvae, but rather prevent the growth thereof beyond the larval or pupal stage. Consequently, the number of adults is substantially reduced. The juvenile hormone mimics actually cause several differnt situations, all of which result in controlling insect population. First of all, most of the treated larvae do not reach adulthood. Thus, the larvae survive for a period of time (possibly an entire growing season) as either larvae or pupae, and then die. During that period the larvae are, of course, very susceptible to predation and injurious climatic conditions. Furthermore, they are themselves incapable of reproduction, thus reducing the insect population for the next growing season. Secondly, some of the treated larvae may develop to various stages of adulthood. For example, the adult insect may only partially eclose, i.e., emerge from the larval or pupal shell. On the other hand, full eclosion may occur but the adult insect is either malformed or dead. In either case, the population of adult insects is substantially reduced.

The growth-inhibiting compounds have many advantages over insecticides and the like. First, the growth-inhibitors do not yield unwanted ecological side effects. Secondly, since the growth inhibitors act as juvenile hormone mimics, the insects do not develop a tolerance to the compounds. Thus, the compounds will not eventually become ineffective. Third, the growth-inhibiting compounds are not harmful to beneficial insects or mammals because they are quite specific for a particular kind of insect.

I have discovered that certain compounds are effective growth inhibitors for mosquito larvae. In the process of the invention any one of these compounds is applied in a growth-inhibiting amount to the habitat of the mosquito larvae, e.g., added to the water wherein the larvae are present. As a result, the growth of the mosquito larvae beyond the larval or pupal stage is inhibited so that few, if any, adult mosquitoes are formed.

THE COMPOUNDS OF THE INVENTION

The compounds used in accordance with the invention fall into four categories as follows:

Group I. Poly-t-butyl-2-cinnamylphenols of the structure

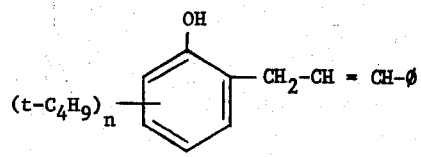

wherein $n$ is 2 or 3.

Illustrative examples of compounds included in Group I are:
3,4-di-t-butyl-2-cinnamylphenol
4,5-di-t-butyl-2-cinnamylphenol
5,6-di-t-butyl-2-cinnamylphenol
3,5-di-t-butyl-2-cinnamylphenol
3,6-di-t-butyl-2-cinnamylphenol
4,6-di-t-butyl-2-cinnamylphenol
3,4,5tri-t-butyl-2-cinnamylphenol
4,5,6-tri-ti-butyl-2-cinnamylphenol
3,4,6-tri-t-butyl-2-cinnamylphenol
3,5,6-tir-t-butyl-2-cinnamylphenol Group II. Poly-t-butyl-4-cinnamylphenols of the structure

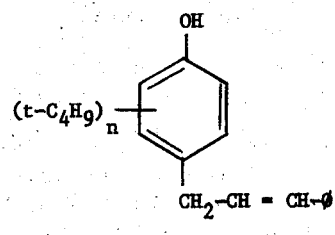

wherein $n$ is 2 or 3.

Illustrative examples of compounds included in Group II are:
2,3-di-t-butyl-4-cinnamylphenol
2,5-di-t-butyl-4-cinnamylphenol
2,6-di-t-butyl-4-cinnamylphenol
3,5-di-t-butyl-4-cinnamylphenol
3,6-di-t-butyl-4-cinnamylphenol
5,6-di-t-butyl-4-cinnamylphenol
2,3,5-tri-t-butyl-4-cinnamylphenol
2,3,6-tir-t-butyl-4-cinnamylphenol
3,5,6-tri-t-butyl-4-cinnamylphenol Group III. Poly-t-butyl-2-dihydrocinnamylphenols of the structure

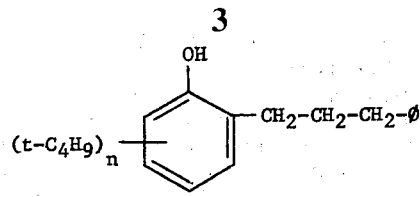

wherein *n* is 2 or 3.

Illustrative examples of compounds included in Group III are:
3,4di-t-butyl-2-dihydrocinnamylphenol
4,5-di-t-butyl-2-dihydrocinnamylphenol
5,6-di-t-butyl-2-dihydrocinnamylphenol
3,5-di-t-butyl-2-dihydrocinnamylphenol
3,6di-t-butyl-2-dihydrocinnamylphenol
4,6-di-t-butyl-2-dihydrocinnamylphenol
3,4,5-tri-t-butyl-2-dihydrocinnamylphenol
4,5,6-tri-t-butyl-2dihydrocinnamylphenol
3,4,6-tri-t-butyl-2-dihydrocinnamylphenol
3,5,6-tri-t-butyl-2-dihydrocinnamylphenol Group IV. Poly-t-butyl-4-dihydrocinnamylphenols of the structure.

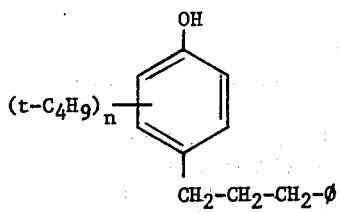

wherein *n* is 2 or 3.

Illustrative examples of compounds included in Group IV are:
2,3-di-t-butyl-4-dihydrocinnamylphenol
2,5-di-t-butyl-4-dihydrocinnamylphenol
2,6-di-t-butyl-4-dihydrocinnamylphenol
3,5di-t-butyl-4-dihydrocinnamylphenol
3,6di-t-butyl-4-dihydrocinnamylphenol
5,6di-t-butyl-4-dihydrocinnamylphenol
2,3,5-tri-t-butyl-4-dihydrocinnamylphenol
2,3,6-tri-t-butyl-4-dihydrocinnamylphenol
3,5,6-tri-t-butyl-4-dihydrocinnamylphenol

PREPARATION OF THE COMPOUNDS

The compounds of Group I may be prepared by refluxing a mixture of cinnamyl alcohol and the appropriate poly-t-butylphenol (wherein at least one position ortho to the hydroxy group is unsubstituted) in aqueous formic acid. For example, the preferred compound in Group I (4,6-di-t-butyl-2-cinnamylphenol) can be prepared by reacting 2,4-di-t-butylphenol with cinnamyl alcohol under reflux in aqueous formic acid. This synthesis is described in my copending application Ser. No. 561,583, filed Mar. 24, 1975, the disclosure of which is included herein by reference. It should be noted that although the compounds of Group I are described in Ser. No. 561,583, there is no disclosure or suggestion in that application that these compounds would inhibit growth in mosquito larvae.

The compounds of Group II are new compounds. They may be prepared in a manner similar to that used for the compounds of Group I. Thus, the appropriate poly-t-butylphenol (wherein the position para to the hydroxy group is unsubstituted) is mixed with cinnamyl alcohol and aqueous formic acid and refluxed. For example, the preferred compound of Group II (2,6di-t-butyl-4-cinnamylphenol) can be prepared by reacting 2,6-di-t-butylphenol with cinnamyl alcohol under reflux in the presence of aqueous formic acid. The synthesis is illustrated by the following formulas:

2,6-di-t-butylphenol

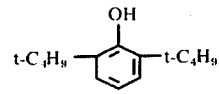

+

Cinnamyl alcohol    HO—CH$_2$—CH=CH—$\phi$

↓ aq. formic acid reflux 2,6-di-t-butyl-4-cinnamylphenol

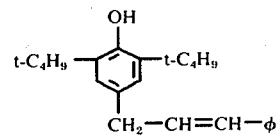

The compounds of Groups III and IV are also new compounds. They can be prepared from the compounds of Group I or II, respectively, by catalytic hydrogenation. This results in hydrogenation of the double-bond in the cinnamyl moiety, thus converting the cinnamyl group (—CH$_2$—CH=CH—$\phi$) into the dihydrocinnamyl group (—CH$_2$—CH$_2$—CH$_2$—$\phi$). For example, the catalytic hydrogenation of 2,6-di-t-butyl-4-cinnamylphenol yields 2,6-di-t-butyl-4-dihydrocinnamylphenol. Thus:

2,6-di-t-butyl-4-cinnamylphenol

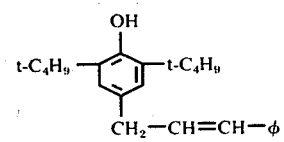

↓ catalytic hydrogenation 2,6-di-t-butyl-4-dihydrocinnamylphenol

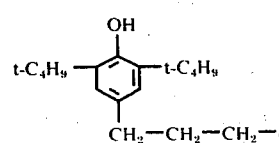

The process of the invention is highly effective in inhibiting the growth of mosquito larvae. Generally, the invention is practiced by applying one of the compounds described above to the breeding place of the mosquito in an amount effective to inhibit growth of the larvae. A preferred procedure is to apply the compound to the body of water wherein the mosquito larvae are located. The concentration of the compound required to achieve growth inhibition will vary depending on the activity of the selected compound. In any particular case the appropriate amount to use can readily be determined by pilot tests well-known to entomologists. In many cases good results have been attained where the compounds are applied in a concentration of about 0.1 to 1 ppm. in bodies of water where the mosquito larvae exist. The growth inhibitors of the invention are effective only on mosquito larvae; they have no effect on adult mosquitoes and consequently must be administered to the larvae to attain the desired result of growth inhibition.

Because the compounds of the invention are effective in very minor concentrations, it is preferred that they be dissolved or suspended in a carrier prior to application to the breeding centers. The solution or suspension increases the bulk, and thus makes it easy to administer small amounts of the compounds to the mosquito breeding area. Solvents appropriate for the purpose should be volatile ones, such as acetone, ethyl ehter, ethanol, benzene, xylene, petroleum naphtha, and the like.

It is within the compass of the invention to use a single compound as herein described or mixtures of two or more of these compounds.

EXAMPLES

The invention is further demonstrated by the following illustrative examples.

EXAMPLE 1

Preparation of 4,6-Di-t-butyl-2-cinnamylphenol

A mixture of 2,4-di-t-butylphenol (206 g.) and cinnamyl alcohol (134 g.) in 88% formic acid (600 ml.) was refluxed for 1.5 hours. Warm water (1 liter) was added to the mixture and the oily layer which formed at the top was collected. This material was distilled and the fraction boiling between 200°–202°C. at 0.05 mm. of Hg was collected (143 g.). On cooling, this material crystallized and the solid was recrystallized from methanol to give colorless prisms, m.p. 89°C. The nuclear magnetic resonance (nmr) spectrum of 4,6di-t-butyl-2-cinnamylphenol at 100 MHz in deuterated chloroform (CDCl$_3$) exhibited absorbances as follows: a singlet (9 protons) at $\delta$ 131, a singlet (9 protons) at $\delta$ 1.42, a doublet (2 protons) at $\delta$ 3.55 (coupling constant = J = 6.0 Hz), a singlet (1 proton) at $\delta$ 5.09, a multiplet (2 protons) at $\delta$ 6.20–6.67, a doublet (1 proton) at $\delta$ 7.03 (J = 3.0 Hz), and a multiplet (6 protons) at $\delta$ 7.13–7.37.

EXAMPLE 2

Preparation of 2,6-Di-t-butyl-4-cinnamylphenol

Cinnamyl alcohol (134 g.) was added to a suspension of 2,6-di-t-butylphenol (206 g.) in 88% aqueous formic acid (470 ml.) and glacial acetic acid (200 ml.), and the mixture was refluxed for 1.5 hours. Warm water (2000 ml.) was added and the oily layer which formed on top of the mixture was collected. The oil was distilled and gave a fraction (179 g.), b.p. 190°–200°C. at 0.5 mm Hg. The oil crystallized upon treatment with Skelly F (a mixture of petroleum hydrocarbons boiling between 30°–60°C.) to give glistening, colorless needles, m.p. 93°C. (Found: C, 85.7; H, 9.20. Calc. for C$_{23}$H$_{30}$O: C. 85.7; H, 9.38). The nuclear magnetic resonance (nmr) spectrum of this compound at 100 MHz in deuterated chloroform (CDCl$_3$) exhibited absorbances as follows: a singlet (9 protons) at $\delta$ 1.41; a singlet (9 protons) at $\delta$ 1.45; a singlet (2 protons) at $\delta$ 3.48; a singlet (1 proton) at $\delta$ 5.07; a multiplet (2 protons) at $\delta$ 6.18–6.58; and a multiplet (7 protons) at $\delta$ 6.96–7.46.

EXAMPLE 3

Preparation of 4,6-Di-t-butyl-2-dihydrocinnamylphenol 4,6-Di-t-butyl-2-cinnamylphenol (11.0 g., prepared as described in Example 1) was hydrogenated at room temperature and pressure in tetrahydrofuran (100 ml.) in the presence of 5% palladium on charcoal. The reaction was allowed to proceed until uptake of hydrogen ceased. The mixture was filtered and the filtrate evaporated to an oil. Distillation of the oil gave the desired compound as a colorless oil, b.p. 186°–187°C. at 0.5 mm. Hg. The nmr spectrum at 100 MHz in CDCl$_3$ exhibited absorbances as follows: a singlet (9 protons) at $\delta$ 1.30, a singlet (9 protons) at $\delta$ 1.43, a multiplet (2 protons) at $\delta$ 1.85–204, a multiplet (4 protons) at $\delta$ 2.50–2.80, a singlet (1 proton) at $\delta$ 4.58, a doublet (1 proton) at $\delta$ 6.99 (J = coupling constant = 2.0 Hz), and a multiplet (6 protons) at $\delta$ 7.13–7.36.

EXAMPLE 4

Preparation of 2,6-Di-t-butyl-4-dihydrocinnamylphenol 2,6-Di-t-butyl-4-cinnamylphenol (30 g., prepared as described in Example 2) was catalytically hydrogenated at room temperature and pressure in tetrahydrofuran (100 ml.) in the presence of 5% palladium on charcoal. The reaction was allowed to proceed until uptake of hydrogen ceased. The mixture was filtered and the filtrate was evaporated to an oil. Distillation of the oil gave the desired compound (25 g.) as an oil, b.p. 195°–200°C. at 10.5 mm. Hg. The nmr spectrum in CDCl$_3$ at 100 MHz exhibited absorbances as follows: a singlet (9 protons) at $\delta$ 1.40, a singlet (9 protons) at $\delta$ 1.43, a multiplet (2 protons) at $\delta$ 1.75–2.10, a multiplet (4 protons) at $\delta$ 2.43–2.82, a singlet (1 proton) at $\delta$ 5.00, a singlet (2 protons) at $\delta$ 6.98, and a multiplet (5 protons) at $\delta$ 7.08–7.40.

EXAMPLE 5

Growth-inhibition Tests

The compound to be tested was added to one liter of water until the final concentration thereof was a growth-inhibiting amount. Fifty early fourth-stage larvae of the common malaria mosquito (*Anopheles quadrimaculatus*) were placed on this water. Larval food was administered daily. Dead larvae and pupae were removed, counted, and discarded daily. Live pupae were removed, rinsed, and transferred to a cup of distilled water. The cup was placed in an emergence cage, and the emerging adults, if any, were maintained on a sugar-water diet.

Two days after the last pupation, the pupal cups were observed for the number of dead pupae and the number of adults that were dead, unable to complete eclosion, or malformed. The effectiveness of the compound in inhibiting growth was determined by adding the number of dead larvae and pupae and the number of adults that were dead, unable to complete eclosion, and malformed. This sum was corrected by Abbott's formula (to adjust for the number of larvae or pupae which would die naturally) and designated as the GI (growth inhibition). The results are expressed as GI-90, i.e., the concentration of growth inhibitor in ppm. that would prevent and/or retard growth in 90% of the treated larvae.

The compounds studied and the results obtained are summarized below:

| Compound | GI-90 (ppm.) |
|---|---|
| 4,6-Di-t-butyl-2-cinnamylphenol | 0.15 |
| 2,6-Di-t-butyl-4-cinnamylphenol | 0.16 |
| 4,6-Di-t-butyl-2-dihydrocinnamylphenol | 0.89 |
| 2,6-Di-t-butyl-4-dihydrocinnamylphenol | 0.60 |

For the purpose of comparison the above-described test was applied to 4t-butyl-2-cinnamylphenol, 2-t-butyl-4-cinnamylphenol, 4-methyl-6t-butyl-2-cinnamylphenol, and 4-t-butyl-2-dihydrocinnamylphenol. The tests demonstrated that these compounds were ineffective in inducing growth inhibition in mosquito larvae.

Having thus described the invention, what is claimed is:

1. A method of inhibiting growth of mosquito larvae, which comprises
    applying to said larvae an effective growth-inhibiting amount of a compound of the structure

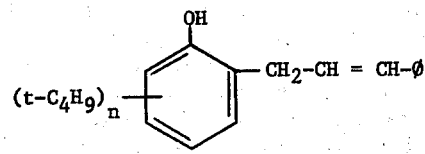

wherein $n$ is 2 or 3.

2. The method of claim 1 wherein the said compound is applied by adding it to the body of water in which the larvae are located.

3. The method of claim 1 wherein the compound is 4,6-di-t-butyl-2-cinnamylphenol.

4. A method of inhibiting growth of mosquito larvae which comprises
    applying to said larvae an effective growth-inhibiting amount of a compound of the structure

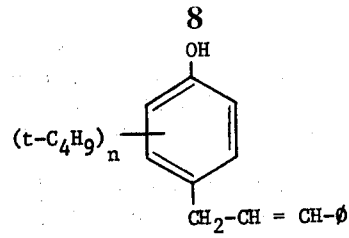

wherein $n$ is 2 or 3.

5. The method of claim 4 wherein the said compound is applied by adding it to the body of water in which the larvae are located.

6. The method of claim 4 wherein the compound is 2,6-di-t-butyl-4-cinnamylphenol.

7. A method of inhibiting growth of mosquito larvae, which comprises
    applying to said larvae an effective growth-inhibiting amount of a compound of the structure

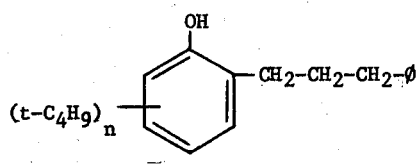

wherein $n$ is 2 or 3.

8. The method of claim 7 wherein the said compound is applied by adding it to the body of water in which the larvae are located.

9. The method of claim 7 wherein the compound is 4,6-di-t-butyl-2-dihydrocinnamylphenol.

10. A method of inhibiting growth of mosquito larvae, which comprises
    applying to said larvae an effective growth-inhibiting amount of a compound of the structure

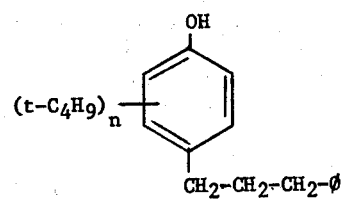

wherein $n$ is 2 or 3.

11. The method of claim 10 wherein the said compound is applied by adding it to the body of water in which the larvae are located.

12. The method of claim 10 wherein the compound is 2,6-di-t-butyl-4-dihydrocinnamylphenol.

* * * * *